United States Patent [19]

Vandevelde et al.

[11] Patent Number: 5,399,555
[45] Date of Patent: Mar. 21, 1995

[54] METHODS OF DISINFECTING, DISINFECTANTS AND PHARMACETICAL COMPOSITION COMPRISING AZOIC COMPOUND

[75] Inventors: Michel Vandevelde; Héléne Margery, both of Rhode-Saint-Genése, Belgium

[73] Assignee: Previsan S.A., Luxembourg, Luxembourg

[21] Appl. No.: 947,090

[22] Filed: Sep. 17, 1992

Related U.S. Application Data

[63] Continuation of Ser. No. 568,868, Aug. 17, 1990, abandoned.

[30] Foreign Application Priority Data

Apr. 19, 1990 [BE] Belgium ............... 09000435

[51] Int. Cl.$^6$ ............. B61K 31/655; C07C 281/20
[52] U.S. Cl. .................................. 514/150; 534/886
[58] Field of Search ................ 514/150; 534/886

[56] References Cited

U.S. PATENT DOCUMENTS

| | | | |
|---|---|---|---|
| 1,958,370 | 5/1934 | Schmelkes et al. | 514/150 |
| 2,073,256 | 3/1937 | Schmelkes et al. | 514/150 |
| 2,263,948 | 11/1941 | Halvorson et al. | 514/150 |
| 2,521,358 | 9/1950 | Galvin | 514/150 |
| 2,903,361 | 9/1959 | Marks et al. | 534/886 X |
| 3,225,026 | 12/1965 | Huibers et al. | 534/886 X |
| 3,637,650 | 1/1972 | Doering | 534/886 X |
| 3,655,391 | 4/1972 | Merli et al. | 534/886 X |
| 3,684,713 | 8/1972 | Piccolini | 252/47.5 |

FOREIGN PATENT DOCUMENTS

| | | |
|---|---|---|
| 0196185 | 10/1986 | European Pat. Off. |
| 0240098 | 10/1987 | European Pat. Off. |
| 0285357 | 10/1988 | European Pat. Off. |
| 0307914 | 3/1989 | European Pat. Off. |
| 2612515 | 9/1988 | France |
| 9001935 | 3/1990 | WIPO |

OTHER PUBLICATIONS

Oser et al., "Studies of the Safety of Azodicarbonamide as as Flour Maturing Agent"; Toxicology and Applied Pharmacology; vol. 7, pp. 445–472; 1965.

S. S. Block; "Disinfection, Sterilization and Preservation" Lea & Febiger; 3rd Ed.; pp. 172–179; 1983; Philadelphia.

Sies et al.; "Hepatic Calcium Efflux During Cytochrome P-450-Dependent Drug Oxidations at the Endoplasmic Reticulum in Intact Liver"; Proc. Natl.

(List continued on next page.)

*Primary Examiner*—Mary C. Lee
*Assistant Examiner*—Fiona T. Powers
*Attorney, Agent, or Firm*—Watson, Cole, Grindle & Watson

[57] ABSTRACT

Compositions useful in methods of disinfecting contain azoic compounds of the general formula

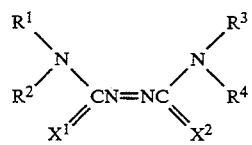

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other. Compositions containing the azoic compounds in a liquid medium at concentrations of from 35 μgr/ml to 2 mgr/ml are sufficient to impede replication and proliferation of viruses of the retrovirus group yet they are insufficiently toxic to destroy sound human or animal cells which come in contact with the compositions. Methods of disinfecting using the compositions are also provided.

12 Claims, No Drawings

OTHER PUBLICATIONS

Acad. Sci. USA; vol. 78; No. 6 pp. 3358–3362; Jun. 1981.
Edited by Reynolds; "Disinfectants and Antispetics"; Martindale The Extra Pharmacopoeia; The Pharmaceutical Press; London; 1982, p. 558–Chloroazodin.
Jentsch et al.; "Inhibition of Human Immunodeficiency Virus Type I Reverse Trascriptase by Suramin–Related Compounds"; J. Gen. Virol.; pp. 2183–2192; May 1987.
Kumler; "The Dipole Moments, Ultraviolet Spectra of Azo–Bis–(Chloroformamidine) and Azo–Bis–(Nitroformamidine)"; Journal of the American Chemical Society, vol. 75; pp. 3092–3093; 1953.
Resnick et al.; "Stability and Inactivation of HTLV–111/LAV Under Clinical and Laboratory Environments"; Jama; vol. 255, No. 14; pp. 1887–1891; Apr. 11, 1986.
Spire et al.; "Inactivation of Lymphadenopathy Associated Virus by Chemical Disinfectants"; The Lancet; pp. 899–901; Oct. 20, 1984.
Martin et al.; "Disinfection and Inactivation of the Human T Lymphotropic Virus Type III/Lymphadenopathy–Associated Virus" The Journal of Infectious Diseases; vol. 152; 400–403; Aug. 1985.
Kosower et al.; "Diamide. A New Reagent for the Intracellular Oxidation of Glutathione to the Disulfide"; Biochemical and Biophysical Research Communications; vol. 37, No. 4, pp. 593–596; 1969.
Schmelkes et al.; "N,N'–Dichloroazodicarbonamidine (Azochloramid), an N–Chloro Derivative Oxidant In and . . . "; Journal of the American Chemical Society vol. 56 pp. 1610–1612; 1934.
Huraux et al.; "Virologie"; Flammarion Medecine Sciences; p. 305; 1985.
Schulhafer et al.; "Acquire Immunodeficiency Syndrome: Molecular Biology and its Therapeutic Intervention (Review)"; In Vivo 3 (2): pp. 61–78; (1989).
Miller et al.; "Genital Mucosal Transmission of Simian Immunodeficiency Virus: Animal Model for Heterosexual Transmission of . . ." Journal of Virology; pp. 4277–4284; Oct. 1989.
D'Agay et al.; "Syndrome Immuno Deficitaireacquis"; Doin Editeurs; $2^e$ edition; pp. 183–184; 1986.
Walker et al. "Inhibition of human immunodeficiency virus . . . " Proc. Nat'l. Acad. Sci. USA, vol. 84 pp. 8120–8124, Nov. 1987.
LePage et al. "Postnatal Transmission of HIV from Mother to Child" The Lancet, Aug. 15, 1987 p. 400.
Hanson, et al.; "Chemical Inactivation of HIV on Surfaces"; BMJ, vol. 298; pp. 862–864; Apr. 1, 1989.
Weir et al, "Diamide Inhibits Pulmonary Vasoconstriction Induced by Hypoxia or Prostaglandin $F_{26}$", Proc. Soc. Exp. Biol. Med., 173(1), 96–103, 1983.
Biochemicals, Organic Compounds for Research and Diagnostic Reagents, Sigma Chemical Company, 1990, Product Number D 3648 (Diamide).

METHODS OF DISINFECTING, DISINFECTANTS AND PHARMACETICAL COMPOSITION COMPRISING AZOIC COMPOUND

This is a continuation of application Ser. No. 568,868, filed Aug. 17, 1990, now abandoned.

The present invention relates to azoic derivatives and to pharmaceutical and disinfectant compositions containing these derivatives.

The retroviruses are defined according to the invention as viruses wherein the genetic material carried on a chain of ribonucleic acid is transcribed inside a target cell of desoxyribonucleic acid by means of an enzyme called reverse transcriptase.

These viruses are responsible for pathologies in the vegetal and animal worlds. A non-exhaustive list of said viruses is to be found in J. M. HURAUX et al., Virologie, Flaremarion Medecine-Science, 1985, Paris.

When the integration stage in the target cell chromosomes has been reached, the recovery likelihoods (return to the previous condition) are low. As a matter of fact, these viruses infect cell series of various types and no drug able to extract the vital genetic material from infected cells seems to be probable at the present time.

Besides, these viruses have mutation properties and they are screened by animal pools which allow them to occur as new antigenic forms (by use of cellular fragments of the host cell, for example), which causes the vaccination to be complex.

To-day, only one treatment is known, which extends the survival of the patients, however not allowing a cure. This treatment comprises administration of 3'-azido-3'-desoxythymidine (see EP-A-196185). This substance acts by reverse transcriptase inhibition.

Other substances are known as inhibiting replication of viruses HIV through their action on the reverse transcriptase. Some didesoxynucleotides (see EP-A-307914) may be, for example, cited.

It has also been found that some substances have as an effect to block the penetration of the viruses into the cells. As substances having this effect, it may be cited for example oligosaccharides or polysaccharides (see EP-A-240098) or also castonospermine (B. D. WALKER, Inhibition of human Immunodeficiency virus suncytium formation and virus replication by castonospermine, Proc. Natl. Acad. Sci. USA, vol. 84, p. 8120–8124, Nov. 1987).

According to these treatments, it may be hoped that the virus having infected a patient will not follow its development and its propagation. However, the patient does not return to this condition before the affection because the provirus is not affected and it subsists inside the cell which has been previously attacked. The treatment is thus palliative and not curative.

This kind of treatment has the important danger to allow resistance of viruses to compounds to appear. It seems already established that the virus becomes resistant to 3'-azido-3'-desoxythymidine after a more or less long term, in particular after about 12 to 18 months (SCHULHAFER E. et al., Acquired immunodeficiency syndrome . . . , In Vivo 3(2): 61–78(1989)).

Finally, it has already been considered to use, as a drug against retroviruses, some benzidine derivatives which bear amongst others azoic groups (see FR-A-2612515). However, in this document there is only a simple affirmation concerning the activity of these compounds.

The transmission way of the viruses have been determined in case of a direct blood contact and contact through wounds by infected material. The risk of a transmission from infected objects and particularly medical material is not to be neglected.

On the other hand, the sexual transmission and the transmission to children via infected mother's milk are also established, which shows that the passage of infecting particles through sound mucosas is possible. (P. LEPAGE et al., Postnatal Transmission of HIV from Mother to Child, The Lancet, Aug. 15, 1987, p. 400; C. J. MILLER et al., Genital Mucosal Transmission of Simian Immunodeficiency Virus, Journal of Virology, Oct. 1989, pp. 4277–4284).

The existence of a virus, inoculation by way of a simple contact, i.e. through skin or mucosa, seems more and more likely. According to the opinion of some searchers, the inoculated viruses would seem to go through a replication phase during which they remain in the area of the mucosa or skin of the carrier. This phase could continue for several months. It would be in the second phase only that the viruses and/or the constituents thereof would spread from the mucosa. (R. ZITTOUN, Syndrome Immuno Déficitaire Acquis, Doins Editeurs, Paris, 1986, p. 183–184).

Thus for the eradication of the disease, it is appeared as necessary to prepare molecules able to disinfect inanimated surfaces and objects, as well as materials and products which come into contact with mucosa and skin. It is appeared as essential to impede as far as possible the retrovirus transmission from a carrier to a healthy person.

Compositions and a method for disinfecting, which use natural or synthetic oliosaccharides or polysaccharides having at least one S-oxoacid group, are already known (see EP-A-285357). However, from the Examples, it results clearly that, even if these compositions are active against the retroviruses, a part of the treated viruses always subsist, with the enormous risk to see after a term the generation of a still more dangerous resistant virus population.

In an international patent application WO-A-90/01935, products are already provided, which are able to come locally into contact with skin, mucosas or body secretions, these products comprising an agent active against the viruses of the retrovirus group, for example sodium suramine, as well as some complex azoic derivatives such as pyridium, neotropine, Congo red, trypan blue, trypan red and trypan violet.

The action of usual chemical disinfectants, such as ethanol, glutaraldehyde, sodium hypochlorite, formalin, β-propiolactone, methylated spirit amongst others, has been examined against retroviruses. (V. B. SPIRE et al., Inactivation of Lymphadenopathy associated virus by chemical disinfectants, The Lancet, Oct. 20, 1984, pp. 899–901; L. RESNICK et al., Stability and inactivation of HTLV-III/LAV under clinical and laboratory environments, JAMA, Apr. 11, 1986, Volume 255, n° 14; L. S. MARTIN et al., Disinfection and inactivation of the human T lymphotropic Virus type III/-lymphadenopathy-associated virus, The Journal of Infectious Diseases, Vol. 152, n° 2, August 1985; P. J. V. HANSON et al., Chemical inactivation of HIV on surfaces, Br. Med. J., 1989, 198: 862–4).

It results from these assays that most of the disinfectants used in hospitals are inefficacious or not very efficient against retroviruses HIV, and consequently potentially dangerous. Those which are the most efficient require rather long contact times, sometimes 10 minutes and more, which is concretely difficult to apply for cleaning grounds, tables, for example. Moreover, some of said disinfectants seem lose their effectiveness in the presence of proteinaceous materials or are not of application if they must come into contact with the skin or the mucosa of a living body, due to their chemical agressivity or their cellular toxicity.

Consequently, the present invention has for its object to provide an active agent against the viruses, particularly of the retrovirus group, in particular the human immunodeficiency viruses HIV, this agent being able to be radically active on said viruses, preferably with a complete removal of the latter, while maintaining its activity at very low concentrations. Advantagelously, said agent will maintain its active power within a cellular medium, an aqueous medium as well as in the presence of organic, particularly proteinaceous materials. Its toxicity will preferably be low. According to a preferred embodiment, the virucidal action will be very rapid against the viruses HIV.

The invention has also for its object to provide a pharmaceutical composition allowing the treatment or prophylaxis of vital diseases.

The invention has also for its object to prepare a composition for disinfecting inanimate objects against viruses.

It is obvious that, according to its applications, either as active substance in a pharmaceutical composition, or as disinfecting agent in a cleaning product, a cosmetical composition or other products of this kind, the active agent will have to meet different requirements concerning solubility, toxicity or stability. It will be the same if application of the pharmaceutical composition must be made orally, parenterally, intravenously, topically or following another administration way, or if the disinfection concerns inanimate objects such as instruments or grounds, or on the contrary organic wastes or liquids to be absorbed.

Suprisingly, it has been found that some azoic compounds are able to particularly effectively and radically play the part of the searched active agent.

To solve the raised problems, it has been provided, according to the invention, azoic derivatives having the general formula:

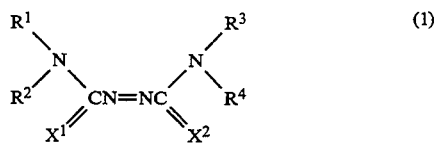

wherein $R_1$ to $R_4$ are identical or different and each represent an atom of hydrogen or halogen, or a substituted or not, aliphatic or aromatic hydrocarbon radical, comprising from 1 to 6 carbon atoms; $X_1$ and $X_2$ are identical or different and each represent an oxygen atom or a $NR_5$ group, in which $R_5$ is a hydrogen or halogen atom, an aliphatic or aromatic hydrocarbon radical comprising from 1 to 6 carbon atoms or a nitro group; $R_5$ when two $NR_5$ groups are simultaneously present, may have an identical or different meaning in each of said groups, and $R_5$ having a meaning other than an atom of chlorine simultaneously in both $NR_5$ groups when $R_1$ to $R_4$ represent hydrogen, as well as their salts, esters and isomers, as therapeutically active substances.

According to the invention, in these derivatives, $R_1$ to $R_5$ may advantageously represent independently a lower aliphatic hydrocarbon radical, in particular a methyl, ethyl, propyl or butyl group. Benzyl groups may also be provided. In the compounds according to formula 1, the halogen atoms are in particular those of chlorine, bromine, iodine and fluorine.

As azoic derivatives according to the invention, one may in particular consider 1.1'-azobisdimethylformamide, 1.1'-azobisformamidine, 1.1'-azobisdimethylformamide, 1.1'-azobisnitroformamidine.

It has to be understood that the invention is not limited to 1.1'-derivatives and that those in 2.2'-position are also included in the invention, as well as all the isomers and their mixtures.

Preparation of 1.1'-azobisformamidine and 1.1'-azobisformamide has already been carried at the end of the last century by J. THIELE (see The Merck Index, 10 ed., 919, Rahway, 1983; F. C. SCHMELKES et al., N,N'-Dichloroazodicarbonamidine (azochloramide), an N-chloro derivative of the oxidant in an oxidation-reduction system, Journal of American Chemical Society, 56, 1610, 1934). 1.1'-Azobisformamide has been known as an adjuvant in food flour. 1.1'-Azobisdimethylformamide has also been known for a long time due to its intracellular oxidising action on human blood cell glutathione (N. S. KOSOWER et al., Diamide, a new reagent for the intracellular oxidation of glutathione to the disulfide, Biochemical and Biophysical Research Communications, vol. 37, n° 4, 1969). 1.1'-Azobisnitroformarmidine has also been known from a long time. (W. D. KUMLER, The Dipole Moments, Ultraviolet spectra and structure of azo-bis-(chloroformamidine) and azo-bis-(nitroformamidine), Journal of American Chemical Societey, 75, 3092, 1953). It is clearly apparent from the documents of this state of the art that it has been fully unexpected to obtain the searched effect from these relatively simple substances which are unexpensive to manufacture and known for a very long time.

A still more unexpected effect has been seen. It is appeared that some derivatives have a selective toxicity against cells infected by HIV virus, while the Supt-1 celles and the lymphocyte cells of the human body are not or only a little altered by the tested compounds. These observations have allowed to consider the possibility of a chemiotherapy which selectively destroys the infected cells while maintaining the sound cells of the patient.

According to the invention, it is thus provided a pharmaceutical composition comprising, as active substance, at least one azoic derivative having the general formula of claim 1 or a salt, ester or isomer which is pharmaceutically acceptable of said derivatives, and at least one pharmaceutically compatible excipient, as well as if necessary one or more pharmaceutically current adjuvants. This composition may be administered as any form, orally or sublingually, rectally or vaginally, by injection or perfusion, topically, transcutaneously or transmucosally, or by any other current form in therapeutical or veterinary medecine. The excipient and possible current adjuvants are selected according to the selected administration way. Advantageously, preservation or solubilization agents, pH neutrality agents, isotonicity agents, buffer agents or other agents may be added to the composition.

The selected excipient or vehicle can be solid or liquid. The composition will be at the option as a powder, ointment, tablets, capsules, aerosols, liquid to be injected and the like.

Also some formulas which release the active substance with late effect can also be provided.

According to an advantageous embodiment of the invention, the pharmaceutical composition according to the invention comprises a disinfectant as a supplement. As a matter of fact, in addition to the curative effect of the composition, it may be advantageous for the virus carrier that the composition defends him against external aggressions which, while stimulating his immunitary defence system, promote the proliferation of the HIV viruses that he carries.

Also according to the invention, the same azoic derivatives having the above-mentioned formula are provided as active substances to combat, on and/or in inanimate objects, with the viruses, in particular of the retrovirus groups, more particularly the HIV human immunodeficiency viruses.

According to the invention, it is also provided compositions to disinfect inanimate objects, containing at least one of these active azoic derivatives as well as a suitable vehicle. As vehicle, one may advantageously provide water or any other suitable solvent in which the active agent is in solution. Other current disinfectant or adjuvant agents can be if necessary provided in supplement.

According to the invention, use of the active azoic derivatives or of above-mentioned disinfection compositions is made for the disinfection of inanimate object against the viruses, in particular the retrovirus group, more particularly HIV human immunodeficiency viruses.

As inanimate objects to be disinfected, use of the present invention can be made, for example with:

plastic, rubber or textile sanitary materials: wadding, absorbent cotton-wool, gauze, bandages, toilet paper, packing films, and the like.

medical, veterinary or dentist instruments and apparatuses: syringues, cannulas, sounds, clips, scissors, stomachal washing kits, surgical tables, basins, and the like.

medical, veterinary or dentist clothes: gloves, dresses, towels, and the like.

cosmetology instruments: material and equipment for hairdresser, manicurist, chiropodist, beautician, and the like.

objects requiring a handling in the alimentary field: feeding-bottles, pans, bottles or cans, in particular for beverages, and the like.

sanitary vehicules: ambulances, rolling tables, and the like.

ground or wall surfaces: quarters or blocks, particularly in hospitals, and the like.

sanitary and hygienic apparatuses: wash-hand basins, urinal vessels, dishes, bath-tubs, and the like.

beverages: water necessary for beverages, milk, and the like.

water for swimming pools.

The disinfection of excrements, wastes of analysis laboratories and particularly of samples taken off from a human or animal body, for example for an analysis, can be provided.

According to the invention, some cosmetic compositions can advantageously be provided in order to include also at least an active azoic derivative of the invention. Obviously in this case, various usual carriers and additives in this field can be applied.

A particular use of an active agent or of an active composition according to the invention can be provided in or on products which can come into contact with the skin or the mucosa of a human or animal body, which optionally is a virus carrier. In or on some of said products, such as physician or dentist gloves, pessaries, contraceptive sheaths, and the like, the active agent or composition can in addition to its disinfecting action form a barrier medium for the transmission of retroviruses from a carrier to a healthy person. For example, it is possible to lubricate a contraceptive rubber sheath with a petrolatum including an active agent according to the invention. For physician gloves, it is also possible to provide two rubber films between which is for example located an amylase amylopectin powder including an active agent according to the invention. In the last case, the disinfecting powder to be used as barrier is thus not in direct contact with the skin.

The disinfection composition according to the invention may also optionally contain a disinfectant agent as a supplement, preferably with a wide spectrum of germicidal action. The so obtained composition has thus an appreciable defense against the presence of pathogenic or allogenic agents, other than retroviruses HIV.

This last property is very important not only due to the important disinfection action such as obtained, but also because it can be useful for the virus carrier himself. As a matter of fact, the latter must avoid as much as possible any activation of his lymphocytar cells. Such an activation, for the HIV carrier, has as an effect the replication of the virus and the proliferation thereof in his cells. A HIV carrier must advantageously follow hygienic life habits in order to avoid at the maximum any risk of infected cell activation and consequently an immunitary reaction of his organism.

By the use of agents and compositions according to the invention, the virus carrier has the possibility to disinfect himself, but also additionally to obtain a protection against immunitary reactions from another source.

The invention will now be illustrated in a more detailed manner by means of some non-limiting examples.

EXAMPLE 1

| Tablets | |
|---|---|
| 1.1'-azobisdimethylformamide | 200-300 mgr |
| Microcristalline cellulose (Avicel PH 101) | 60 mgr |
| Povidone BP | 15 mgr |
| Sodium starch glycolate | 20 mgr |
| Magensium stearate | 5 mgr |
| lactose, q.s. for | 500 mgr |

EXAMPLE 2

| Capsules | |
|---|---|
| 1.1'-azobisformamide | 400-600 mgr |
| Microcrystalline cellulose (Avicel) for one capsule | 50 mgr |

EXAMPLE 3

| Long-release composition (6 to 8 hours) | |
|---|---|
| 1.1'-azobisdimethylformamide | 400-600 mgr |
| Hydroxypropyl methyl cellulose | 111 mgr |
| Lactose | 53 mgr |
| Povidone BP | 28 mgr |

-continued

| Long-release composition (6 to 8 hours) | |
|---|---|
| Magnesium stearate | 7 mgr |

First, hydroxypropyl methyl cellulose is mixed with 1.1'-azobisdimethylformamide, then the other components are added.

EXAMPLE 4

| Injectables | |
|---|---|
| 1.1'-azobisformamide | 10–30 mgr |
| Hydrochloric acid | 0.1M |
| Sodium hydroxide | 0.1M | pH is adjusted to a value of 4 to 7 by means of either the acid or the base, the product is hot dissolved and filtration is made on sterile micropore. The liquid is then poured into brown sterile ampoules.

EXAMPLES 5

| Injectables | |
|---|---|
| 1.1'-azobisformamidine | 50–150 mgr |
| Benzyl alcohol | 10 mgr |
| Glycofurol | 75 mgr |
| Water for injection | 3 ml |

The product is prepared by dissolution of the active substance in glycofurol, then mixing the so obtained solution with filtered water and benzyl alcohol. The whole is poured into a sterile brown ampoule.

EXAMPLE 6

Injectables by intravenous way
1.1'-azobisnitroformamidine 50–150 mgr
Sterile water without pyrogen is added to this component, this water being buffered by a phosphate buffer at pH 7, in order to obtain 25 ml.

EXAMPLE 7

Suppository
To 150–250 gr of micronized powder of 1.1'-azobisformamidine, 2 gr of glycerin are added in order to form a suppository.

Experimental tests have been made by the laboratory of Institut Pasteur of Brabant, Belgium, in order to examine the efficiency of the azoic derivatives according to the invention.

EXAMPLE 8

Starting materials of the test:
1.1'-azobisformamidine of a purity level of 98%. The purity has been examined by a carbon-hydrogen test.
a supernatent of cell cultures (Molt-3) which continuously produce HIV-1 viruses. The used viral supernatent has a reverse transcriptase activity of $1 \times 10^6$ cpm/ml.
cells of a continue human T line of $T_4$ phenotype (Supt-1) cultivated in a RPMI medium, additionally supplied with 10% of foetal calf serum and 1% of glutamine.
The effectiveness of 1.1'-azobisformamidine has been investigated on two aspects:
its toxicity against sound cells
its action on the infectious power of HIV-1 viruses for the Supt-1 line.

(a) Examination of the toxicity against sound cells.

The cellular mortality has been determined by exclusion with trypan blue.

To dilutions of 1/500, 1/1500 and 1/3000, 1.1'-azobisformamidine does not decrease the cellular viability of Supt-1 cells.

(b) Examination of the infectious power.

Viral preparations of HIV-1 of high tiler are incubated in the presence of dilutions of 1.1'-azobisformamidine of 1/500, 1/1500 and 1/3000 and for different incubation periods: 1 minute, 10 minutes and 30 minutes. For the incubation, 0.3 ml of virus concentrate and the active substance are brought together at a double concentration (once for the virus volume and once for the product volume). For 30 minutes at 37° C., the Supt-1 cells are previously treated with 10 μgr/ml of polybren, then they are inoculated with the preparations of treated viruses. As controls, non-inoculated cells and cells inoculated with a non-treated virus preparation are provided.

Then, the infectious power of said preparations is determined, for each cellular passage, the vital production (measure of the expressed p24 antigen) being followed in the solubilized cellular lysates of the examined Supt-1 cells.

The measures of the infectious power of HIV-1 virus after incubation with 1.1'-azobisformamidine appear from the following Table 1, by comparison with a non-infected control and with a control infected by non-treated viruses.

EXAMPLE 9

The starting material for the test differs from that of Example 8 by using 1.1'-azobisdimethylformamide instead of 1.1'-azobisformamidine.

(a) Toxicity examination.

At dilutions at 1/500, 1/1500 and 1/3000, the 1.1'-azobisdimethylformamide does not decrease the cellular viability of the Supt-1 cells.

(b) Examination of the infectious power.

One proceeds in the same way as in Example 8b. The measures of the infectious power of the HIV-1 virus after incubation with 1.1'-azobisdimethylformamide appear from the following Table I.

TABLE 1

| Measure of the infectious power of the HIV-1 on the 14th day after inoculation of Supt-1 cells. | | |
|---|---|---|
| Active substance (dilution) | Duration of the treatment of the viruses | |
| 1.1'-Azobisformamidine | | |
| 1/500 | 1 min | 0.234 ± 0.008 |
| | 10 min | 0.267 ± 0.021 |
| | 30 min | 0.245 ± 0.020 |
| 1/1500 | 1 min | 0.469 ± 0.013 |
| | 10 min | 0.439 ± 0.008 |
| | 30 min | 0.406 ± 0.032 |
| 1/3000 | 1 min | 0.809 ± 0.049 |
| | 10 min | 0.505 ± 0.023 |
| | 30 min | 0.740 ± 0.013 |
| 1.1'-Azobisdimethylformamide | | |
| 1/500 | 1 min | 0.275 ± 0.049 |
| | 10 min | 0.206 ± 0.006 |
| | 30 min | 0.203 ± 0.008 |
| 1.1500 | 1 min | 0.278 ± 0.050 |
| | 10 min | 0.217 ± 0.028 |
| | 30 min | 0.193 ± 0.004 |

TABLE 1-continued

Measure of the infectious power of the HIV-1 on the 14th day after inoculation of Supt-1 cells.

| Active substance (dilution) | Duration of the treatment of the viruses | |
|---|---|---|
| 1/3000 | 1 min | 0.239 ± 0.016 |
|  | 10 min | 0.283 ± 0.042 |
|  | 30 min | 0.198 ± 0.009 |
| Virus control |  | 1.033 ± 0.081 |
| Cell control |  | 0.206 ± 0.005 (optical density 492 nm). |

It is clearly apparent from this Table that at a dilution of 1/500, 1.1′-azobisformamidine protects the Supt-1 cells after a treatment of the viruses for 1 minute only. 1.1′-azobisdimethylformamide has this effect, even at dilutions of 1/3000. For the latter substance, the test has been extended up to the 25th day. The effectiveness of this active substance is maintained for all the dilutions, when the viruses have been treated for 30 minutes.

On the other hand, with a phase-contrast microscope, no cytopathogenic effect was observed for the cells inoculated with virus previously treated with 1.1′-azobisdimethylformamide and 1.1′-azobisformamidine. On the contrary, syncytia appear from the 14th day on after infection with the control viral preparation.

(c) 1.1′-azobisdimethylformamide has moreover been examined concerning its toxicity against cells infected with viruses.

To this end, the cellular mortality has been determined by exclusion with trypan blue.

This examination has been made on Molt-3 cells infected by HTLVIII-B which are producing HIV-1 viruses.

TABLE 2

| Molt-3 cells (HIV-1) | Number of living cells | Number of dead cells | % of dead cells |
|---|---|---|---|
| Controls | 57 | 5 | 8 |
| Cells treated with 1.1′-azobisdiméthylfomamide | | | |
| Dilution / Duration (min.) | | | |
| 1/500  1 | 62 | 9 | 12.7 |
| 10 | 67 | 11 | 14 |
| 30 | 58 | 12 | 17.1 |
| 1/1500  30 | 70 | 15 | 17.6 |
| 1/3000  30 | 58 | 12 | 17.1 |

It results very clearly from the Table 2 that the mortality of the infected cells is doubled in the presence of 1.1-azobisdimethylformamide after 30 minutes of action, even at the dilution of 1/3000, while this molecule shows no toxicity for the human Supt-1 and lymphocyte cellular lines, even after 24 hours.

EXAMPLE 10

The test material is different from that of Example 9 in that 1.1′-azobisdimethylformamide is dosed at a dilution of 1/100 (10 mgr/ml).

(a) Examination of the cellular toxicity against normal cells, namely non-infected cells (Supt-1 line).

The cellular mortality has been determined by exclusion with trypan blue.

TABLE 3

| Supt-1 cells | Duration (hours) | Number of living cells | Number of dead cells | % of dead cells |
|---|---|---|---|---|
| Controls | 0 | 61 | 19 | 24 |
|  | 1 | 57 | 18 | 32 |
|  | 5 | 55 | 20 | 36 |
| Cells treated with 1.1′-azobisdimethyl-formamide (dilution: 1/100) | 0 | 61 | 21 | 26 |
|  | 1 | 63 | 20 | 24 |
|  | 5 | 56 | 22 | 28 |

These results are given by ml of culture which was taken off.

It is clearly apparent from the Table that, even at a relatively high concentration, the 1.1′-azobisdimethylformamide has no toxicity against sound Supt-1 cells.

(b) Examination of the infectious power of the HIV-1 virus.

One proceeds as in Example 8(b) by treating the viruses for 30 minutes with 1.1′-azobisdimethylformamide at a dilution of 1/1000. After inoculation of Supt-1 cells with this viral preparation, the p24 antigens are determined, being expressed by the optical density, after 14, 18 and 21 days.

TABLE 4

| | p24 Antigens expressed by optical density | | |
|---|---|---|---|
| | Day 14 | Day 18 | Day 21 |
| Control cells | 0.125 | 0.126 | 0.168 |
| Control cells infected by HIV | 0.224 | 1.078 | 0.765 |
| Cells + HIV-1 treated by the active substance | 0.144 | 0.160 | 0.130 |

It is apparent from this experience that the HIV treated with 1.1′-azobisdimethylformamide is not able to infect the sound Supt-1 cells.

(c) Examination of the integration of the vital genome into the chromosomic DNA of Supt-1 cells.

By means of a genetic amplification through a thermostable polymerase, the presence of genes "GAG", "LTR" and "ENV" of the HIV-1 provirus is evidenced. This method is called P.C.R. Polymerase chain Reaction) (Chin-Yih Ou et al., Sciences 239, 295–297, 1988).

Said method is applied for detecting HIV-1 provirus in the genome of Supt-1 cells inoculated with HIV-1 virus incubated with 1.1′-azobisdimethylformamide (dilution 1/100), as described in Example 8.

Amplified oligonucleotides, UV visible by means of ethidium bromide appear only in the tubes corresponding to an inoculation with HIV-1 viruses which were not treated with the active substance.

Moreover, after hybridation with specific p32 marked moulds for the three searched genes, it is possible to conclude that HIV-1 provirus is totally absent within Supt-1 cells which have received inoculates of HIV-1 virion treated with a 1/100 dilution of the active substance.

It may thus be deducted that this active substance protects the cells against the infection by HIV-1.

EXAMPLE 11

The test material is different from that of Example 8 in that the used substance is 1.1′-azobisformamide dosed at a concentration of 35 mgr/l, i.e. 35 μgr/ml, namely at an extremely low concentration (obtained by the supernatent of a suspension of 0.5 gr/l in RPMI).

(a) Examination of the cellular toxicity against sound cells.

No toxical effect has been noted for the Supt-1 cells, even after 24 hours of incubation.

(b) Examination of the infectious power.

.One proceeds as in Example 8(b) with incubation periods of the viruses of 15 minutes, 30 minutes, 60 minutes and 120 minutes. No cytopathogenic effect has been observed (no formation of syncytia).

TABLE 5

| p24 Antigens expressed by optical density | | | |
|---|---|---|---|
| | Day 14 | Day 18 | Day 21 |
| Control cells | 0.140 | 0.142 | 0.136 |
| Infected control cells | 1.014 | 1.510 | 0.730 |
| Cells + HIV-1 treated 15 min. | 0.134 | 0.150 | 0.140 |
| Cells HIV-1 treated 30 min. | 0.152 | 0.170 | 0.146 |
| Cells + HIV-1 treated 60 min. | 0.142 | 0.162 | 0.135 |
| Cells + HIV-1 treated 120 min. | 0.145 | 0.168 | 0.154 |

It can thus be concluded that the 1.1'-azobisformamide protects the cellular cultures against the infectious power of HIV-1.

(c) Examination of the integration of the viral genome into chromosomic DNA of Supt-1 cells.

One proceeds as in Example 11(c). The search of genes "GAG", "LTR" and "ENV" has been made in cellular cultures inoculated with a virus incubated for 15 minutes with the active substance. This search is appeared as being negative, and thus it can be concluded that 1.1'-azobisformamide at the dosage of 35 $\mu gr/ml$ protects the cells against infection by HIV-1.

EXAMPLE 12

The absence of toxicity of azobisformamide for the humans has already been described by B. L. OSER et al., Studies of the Safety of Azodicarbonamide as a Flour-Maturing agent, Toxicology and applied Pharmacology 7, 445–472(1965).

Three sound volunteers were treated for 30 days with 1500 mgr a day of azobisformamide in three portions of 500 mgr.

No secondary effect was reported and the hematological parameters remained perfectly normal for the experimental treatment of 30 days.

On the other hand, three patients presenting different stages of AIDS were also treated with azobisformamide in the same dosages as the sound volunteers.

The first patient in final phase presented at least 30 $T_4$ lymphocytes/mm$^3$, abundant diarrheas and a complete space-time disorientation.

The second patient in "ARC" phase presented a lymphocytar $T_4$ population of 190/mm$^3$, in constant decrease, as well as occasional diarrheas and anal herpes.

The third patient was a sound seropositive, he had a population of 350 $T_4$ lymphocytes/mm$^3$ and he had no sign of pathology.

The first patient had on day 0 of the treatment 1850 white corpuscules including 17% of lymphocytes of which 5% presented the $T_4$ receptor (namely 24 cells). On day 30 of the treatment, the white corpuscules were in an amount of 2600 including 20% of lymphocytes of which 9% presented the $T_4$ receptor (namely 49 cells/mm$^3$)., which represented an improvement of 100%. On the other hand, the diarrhea has ended, the patient had recovered his possibility of coherent talking with his near relations, as well as a limited walking autonomy.

The second patient had on day 30 280 $T_4$ lymphocytes/mm$^3$, the diarrhea had completely disappeared as well as the anal herpes.

The third patient has on day 30 440 $T_4$ lymphocytes/mm$^3$.

These results, even if they concern a restricted sampling, are remarkable and surprising and they could in no way be expected by the ones skilled in the art.

EXAMPLE 13

Disinfectant effevescent tablet for 100 cm$^3$ of water.

| 1.1'-Azobisdimethylformamide | 33 mgr |
|---|---|
| Citric acid | 15 mgr |
| Tartaric acid | 17,5 mgr |
| NaH CO$_3$ | 37,5 mgr |
| Avicel PH IC$_2$ | 27 mgr |
| Lactose EFK | 45 mgr |
| For one tablet: 175 mgr | |

EXAMPLE 14

Disinfectant effervescent tablet, for 1000 cm$^3$ of water

| 2.2-Azobismethylformamidine | 330 mgr |
|---|---|
| Citric acid | 150 mgr |
| Tartaric acid | 175 mgr |
| NaHCO$_3$ | 375 mgr |
| Avicel PH IC$_2$ | 180 mgr |
| Lactose EFK | 522.2 mgr |
| Sodium lauryl sulfate | 64 mgr |
| Aerosil 200 | 3.8 mgr |
| For one tablet: 1800 mgr | |

Tooth-paste

To 100 gr of a tooth-paste comprising 4% of ricinilate, 30 mgr of 1.1'-azobisfluoroformamidine (for 30 days) were added.

EXAMPLE 16

| Mouth-wash | |
|---|---|
| Sodium perfluorate | 8 gr |
| Borax | 32 gr |
| Sodium chloride | 20 gr |
| Sodium bicarbonate | 40 gr |
| 1.1'-azobisfluoroformamidine | 30 gr |
| Mint oil | 3 drops |
| 1 coffee spoonful in a lukewarm water cup. | |

EXAMPLE 17

| Cream | |
|---|---|
| 1.1'-Azobisformamide | 1 gr |
| Triethanolamine | 1 gr |
| Glycerol | 2.5 gr |
| White wax | 2.5 gr |
| Stearic acid | 6 gr |
| Almond oil | 7.5 gr |
| Lavender oil | 2 drops |
| Aqua conservans, ad for 50 gr of cream. | 50 gr FMS |

EXAMPLE 18

| Talc | |
|---|---|
| 1.1'-Azobisformamide | 2 gr |
| Lavender oil | 5 drops |
| Talc ad | 100 gr |
| for 100 gr of talc. | |

EXAMPLE 19

| Liquid soap | |
|---|---|
| 1-Monochloro-azobisformamidine | 3 gr |
| Potassium soap | 60 gr |
| Lavender oil | 10 drops |
| Antiseptic solution ad | 100 gr |
| for 100 gr of soap. | |

EXAMPLE 20

Toilet paper, hygienic bands and tampons, wadding and the like.

A powder to be sprayed was first prepared, the composition of which is for example as follows:

| 1.1'-Azobisdimethylformamide | 20 mgr |
|---|---|
| Bismuth sub-gallate | 50 gr |
| Zinc peroxide | 100 gr |
| Talc | 840 gr |
| for 1 kg of powder to be sprayed. | |

This powder which adheres to the fibers of the treated products was then sprayed in a usual way.

EXAMPLE 21

| Oil for preservative sheath | |
|---|---|
| Silicone oil | 100 gr |
| 1.1'-Azobisformamide | 1 gr |

The preservative sheaths are coated with the preparation as well as on the internal face as on the external one.

It has to be understood that the present invention is in no way limited to the hereinabove described embodiments and that many variants may be brought therein without departing from the scope of this invention.

Many other disinfectant of pharmaceutical compositions may be provided in addition to those given as Examples, by simply using the formulations such as used in general in the concerned fields, such as cleaning products, cosmetic compositions, pharmaceutical products and the like.

What is claimed is:

1. A composition comprising:
an active substance selected from one or more azoic compound of the general formula

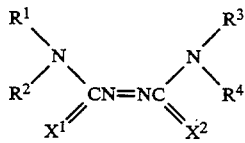

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other; and a liquid medium, wherein said active substance is present in said liquid medium at a concentration of from 35 μgr/ml to 2 mgr/ml.

2. A composition as defined in claim 1, wherein said liquid medium comprises a mouthwash composition.

3. A composition as defined in claim 1, wherein said liquid medium comprises a toothpaste composition.

4. A composition as defined in claim 1, wherein said liquid medium comprises a liquid soap composition.

5. A composition as defined in claim 1, wherein said liquid medium comprises a skin cream composition.

6. A composition as defined in claim 1, wherein said liquid medium comprises a lubricating oil composition.

7. A composition comprising:
an active substance selected from one or more azoic compound of the general formula

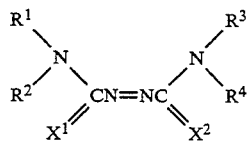

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other; and a liquid medium comprising at least one member selected from the group consisting of pharmaceutically compatible excipients, adjuvants and carriers, wherein the concentration of said compound in said liquid medium is between 35 μgr/ml and 2 mgr/ml.

8. A tablet comprising a composition, said composition comprising an active substance selected from one or more azoic compound of the general formula

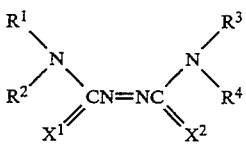

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other; and at least one member selected from the group consisting of pharmaceutically compatible excipients, adjuvants and carriers.

9. A tablet as defined in claim 8, comprising an effervescent agent.

10. In combination, a capsule and a composition within said capsule, said composition comprising an active substance selected from one or more azoic compound of the general formula

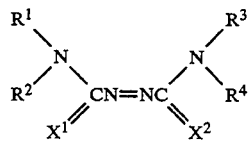

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

11. A suppository comprising an active substance selected from one or more azoic compound of the general formula

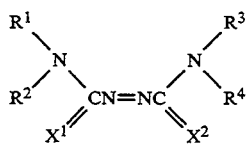

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

12. A powder composition comprising talc and an active substance selected from one or more azoic compound of the general formula

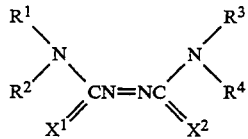

wherein $R^1$, $R^2$, $R^3$ and $R^4$ are identical or different and each represents an atom of hydrogen or an aliphatic or aromatic hydrocarbon radical comprising from 1 to 6 carbon atoms; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other, said active substance being present in said composition at a concentration of at least about two percent by weight.

* * * * *